(12) United States Patent
Surpin et al.

(10) Patent No.: US 7,640,173 B2
(45) Date of Patent: *Dec. 29, 2009

(54) METHOD AND SYSTEM FOR EVALUATING A PHYSICIAN'S ECONOMIC PERFORMANCE AND GAINSHARING OF PHYSICIAN SERVICES

(75) Inventors: Jo Surpin, Philadelphia, PA (US); Michael Kalison, Skillman, NJ (US)

(73) Assignee: Applied Medical Software, Inc., Collingswood, NJ (US)

( * ) Notice: Subject to any disclaimer, the term of this patent is extended or adjusted under 35 U.S.C. 154(b) by 315 days.

This patent is subject to a terminal disclaimer.

(21) Appl. No.: 11/283,309

(22) Filed: Nov. 18, 2005

(65) Prior Publication Data

US 2006/0149596 A1    Jul. 6, 2006

Related U.S. Application Data

(63) Continuation-in-part of application No. 10/346,308, filed on Jan. 17, 2003, now Pat. No. 7,546,245.

(60) Provisional application No. 60/349,847, filed on Jan. 17, 2002.

(51) Int. Cl.
   *G06Q 50/00*      (2006.01)
   *G06Q 40/00*      (2006.01)

(52) U.S. Cl. ............................................. 705/2; 705/35

(58) Field of Classification Search ...................... 705/2
See application file for complete search history.

(56) References Cited

U.S. PATENT DOCUMENTS

| | | | |
|---|---|---|---|
| 5,324,077 A | 6/1994 | Kessler et al. ................. | 283/54 |
| 5,652,842 A | 7/1997 | Siegrist, Jr. et al. ............ | 705/2 |
| 5,784,635 A | 7/1998 | McCallum .................... | 712/32 |
| 5,918,208 A | 6/1999 | Javitt ............................. | 705/2 |
| 5,970,463 A | 10/1999 | Cave et al. ..................... | 705/3 |

(Continued)

OTHER PUBLICATIONS

Steindel, Using outlier events to monitor test turnaround time, Jul. 1999, Arch Pathol Lab Medl;123(7):607-14.*

(Continued)

*Primary Examiner*—C. Luke Gilligan
*Assistant Examiner*—Tran Nguyen
(74) *Attorney, Agent, or Firm*—Porzio, Bromberg & Newman, P.C.

(57) ABSTRACT

The invention relates to a method and system of physician economic performance evaluation in which the relative medical difficulty associated with patients admitted by a particular physician is determined and, given that measurement, judgments made concerning the relative amount of inpatient resources that the physician required. Also, one application of the present invention relates to a method for gainsharing of physician services using a surplus allocation methodology for rewarding physicians in relation to their performance. An incentive pool is determined from previous patient claims and payments made to physicians in advance, such as in a base year. Best practice norms are established for a plurality of classified diagnosis groups. In one embodiment of the present invention, the classified diagnosis related groups are adjusted for severity of illness to compensate for actual clinical challenges faced by individual physicians. The best practice norms can be used in the surplus allocation method for determining physician performance. The incentive is established proportional to the relationship between a physician's individual performance and the best practice norm.

10 Claims, 13 Drawing Sheets

U.S. PATENT DOCUMENTS

| | | |
|---|---|---|
| 6,343,271 B1 | 1/2002 | Peterson et al. .............. 705/4 |
| 2002/0111826 A1* | 8/2002 | Potter et al. .................. 705/2 |
| 2003/0163352 A1 | 8/2003 | Surpin et al. ................. 705/2 |

OTHER PUBLICATIONS

Hardy, The Evolution of Hospitalist Programs, Sep. 2000, Healthcare Financial Management, v 54, n 9, p. 63.*

Martin, Incentives in HMOs, 2001, National Bureau of Economic Research (Cambridge, MA) Working Paper No. 8522.*

Hardy, The Evolution of Hospitalist Programs, Sep. 2000, Healthcare Financial Management, vol. 54, No. 9, p. 63.*

* cited by examiner

\* - 3M software assigns APR-DRG and SOI

Physician Report

Provider Number
Provider Name
Responsible Physician
Medical Improvement Incentive (LOI)
  LoI Breakdown by Severity of Illness     1: $        2: $        3: $        4: $
Surgical Improvement Incentive
Performance Incentive
Total Incentive
Total Cases

| Patient | APR-DRG /SOI | Case Type | Actual LOS | Actual Cost | BP LOS | BP Cost | LOS Opp | Cost Opportunity | Max Perf. Incentive | Performance Incentive |
|---|---|---|---|---|---|---|---|---|---|---|
| 0 | 0452 | Medical | 3 | $2,914 | 5 | $5,854 | 0 | $0 | $96 | $96 |
| 0 | 0532 | Medical | 1 | $1,591 | 5 | $4,438 | 0 | $0 | $73 | $73 |
| 0 | 1413 | Medical | 3 | $2,960 | 6 | $5,511 | 0 | $0 | $91 | $91 |
| 0 | 1941 | Medical | 6 | $5,725 | 4 | $3,496 | 2 | $2,228 | $58 | $28 |
| 0 | 3471 | Medical | 3 | $4,078 | 5 | $4,249 | 0 | $0 | $70 | $70 |
| 0 | 3472 | Medical | 7 | $6,067 | 6 | $5,648 | 1 | $419 | $93 | $85 |
| 0 | 4202 | Medical | 1 | $1,510 | 4 | $4,123 | 0 | $0 | $68 | $68 |
| 0 | 7202 | Medical | 5 | $3,998 | 7 | $6,201 | 0 | $0 | $102 | $102 |

Fig. 7

* - 3M software assigns APR-DRG and SOI

METHOD AND SYSTEM FOR EVALUATING A PHYSICIAN'S ECONOMIC PERFORMANCE AND GAINSHARING OF PHYSICIAN SERVICES

CROSS REFERENCE TO RELATED APPLICATION

This application is a continuation-in-part of U.S. patent application Ser. No. 10/346,308 filed Jan. 17, 2003 now U.S. Pat. No. 7,546,245, which claims priority of U.S. Provisional Patent Application No. 60/349,847 filed Jan. 17, 2002, both of which are hereby incorporated in their entirety by reference into this application.

BACKGROUND OF THE INVENTION

1. Field of the Invention

The invention relates to a method and system of physician economic performance evaluation in which the relative medical difficulty associated with patients admitted by a particular physician is determined and, given that measurement, judgments made concerning the relative amount of inpatient resources that the physician required. Also, one application of the invention relates to a method and system of gainsharing of physician services in which a best practice norm is established for a plurality of classified diagnosis groups and an incentive pool is distributed to physicians by comparing physician performance to the best practice norm while meeting constraints on incentive distribution.

2. Description of the Related Art

Many strategies have been proposed and implemented that were intended to contain the rising cost of health care. For example, over the past decade, health maintenance organizations ("HMOs") have received considerable attention. HMOs employ various strategies to incent and/or penalize health care consumers (enrollees), hospitals and physicians. Physicians are particularly important because they exercise ultimate judgment over medical decision-making. Consequently, HMOs employ a combination of strategies, such as "hands on" review over medical utilization decisions, coupled with discounts on physician fees in order to reduce physician costs, and to control the impact of physicians on other health care costs, such as hospital costs. These strategies are sometimes criticized as being indirect, complex and overly bureaucratic.

A different kind of healthcare cost containment strategy was implemented by Medicare in 1983: In that year, the federal program for the elderly replaced "reasonable cost" reimbursement for acute care hospitals with "payment by the case". Specifically, beginning in 1983, Medicare reimbursed hospitals a fixed price for each Diagnosis Related Group ("DRG"). By reimbursing a fixed price for each DRG, hospitals were furnished economic incentives to reduce resource utilization. The payment system was known as the Medicare Prospective Payment System, or "PPS".

New Jersey acute care hospitals continue to suffer their worst financial distress in recent history. A report issued by the New Jersey Health Care Facilities Finance Authority in June, 1999, suggests that a large part of the problem is New Jersey's Medicare length of stay which was 1.6 days over the national average, at that time. The report estimates that removing the costs associated with these excess days could save $600 million. Improved operational performance by hospitals, however, cannot be achieved without the active collaboration of the doctors. To achieve this necessary partnership, the New Jersey Hospital Association (NJHA) proposes a Demonstration to test whether or not Performance Based Incentives can improve the efficiency and effectiveness of hospital inpatient care for Medicare fee for service beneficiaries.

Under the Medicare Prospective Payment System (PPS), prospective payment by the case referred to as Diagnosis Related Group, DRG provides acute care hospitals with incentives to control unnecessary resource utilization. Diagnosis Related Groups ("DRGs") is a system of patient classification utilized by the federal government to pay hospitals. Under the Medicare Prospective Payment System ("PPS"), DRGs are utilized to pay hospitals a fixed price per case. Physicians, however, exercise ultimate control over such decisions and unfortunately, in this particular regard, the Medicare fee for service payment system that governs the reimbursement for physicians contains financial incentives to provide more services, even when medically unnecessary. Attempts to resolve this conflict of economic incentives have been unsuccessful. Medicare risk-based systems have failed to gain the confidence of both providers and beneficiaries.

Gainsharing has been a primary objective of the healthcare industry for many years. The need to align the economic incentives of hospitals and doctors (any payors) has grown more urgent as the economic fortunes of all parties have deteriorated. Pursued by many, it seemed that the goal was close to realization in the late 90s: Unofficial communication from the Office of Inspector General (OIG) seemed to recognize the importance of taking this next step. These hopes were dashed, however, when the OIG issued a formal statement in 1999 indicating that, while potentially of great value, " . . . regulation of gainsharing arrangements requires clear, uniform, enforceable and independently verifiable standards applicable to all affected parties . . . "

In a seeming reversal of its prior position, on Jan. 11, 2001 the HHS Office of Inspector General (OIG) suggested that it would permit the use of properly structured gainsharing arrangements to reduce hospital operating costs. Although gainsharing arrangements take numerous forms, they most often relate to services furnished within a single clinical specialty (e.g. cardiac surgery or oncology) and are executed directly between a hospital and one of the following individuals or groups: one or more individual physicians providing service in the clinical specialty; one or more group practices composed exclusively of physicians furnishing care in the clinical specialty at the hospital; or a single entity representing all staff or employed physicians furnishing care in the clinical specialty at the hospital.

Gainsharing arrangements typically include several common elements. The hospital contracts with participating independent consultants or physicians to analyze current operational practices within the clinical specialty. These practices include supply use, equipment use, operating room use, ancillary-service use, formulary restrictions, clinical protocols, nonphysician staffing, scheduling of procedures, bed-use review, and discharge assessment.

The physicians are expected to comply with standard policies, procedures, and protocols that reflect best practices as determined by clinical consultants. These best practices are reviewed and revised, as necessary, by physicians practicing in the clinical specialty to ensure that they are consistent with quality care. Any reduction in operating costs in the clinical specialty is documented by the hospital over a specified period after implementation of the best practices. The hospital then monitors whether the participating physicians meet mutually agreed-upon, objective benchmarks called quality safeguards for quality of care and patient satisfaction. Finally, if such quality safeguards are met, the participating physicians are paid a fixed percentage of the reduction in operating costs associated with implementation of the best practices.

It is desirable to provide an improved method and system for evaluating physician performance which can be the foundation for various cost containment strategies, such as gainsharing of physician services.

SUMMARY OF THE INVENTION

Conventionally, diagnosis related group classifications have been used to determine of fixed price per case to pay hospitals. The present invention applies classified designated groups to physicians to evaluate physician economic performance. The physician economic performance can be determined by a comparison of relative resource consumption among physicians, given a certain type of classified patient DRG, which can be adjusted for severity of illness (SOI). The SOI adjustment is advantageous in fairly determining economic performance of physicians, because individual physicians may attract a more difficult case mix because of skill or reputation.

It was found that a successful healthcare cost containment strategy (PPS, HMO, or other) begins with the physician who is the medical decision maker. The present invention involves the first step in that strategy, physician performance evaluation, as well as its application, for example, incentive based compensation. The present invention provides a methodology for evaluating the relative consumption of inpatient resources of individual physicians, adjusted for case-mix, and severity of illness. Physician economic performance can be evaluated utilizing classified DRGs uniquely sensitive to the varying medical difficulty presented by cases within a DRG category, such as All Patient Refined Diagnosis Related Groups or other systems of patient classification that is adjusted for severity of illness. Accordingly, the present invention can evaluate the relative medical difficulty associated with the patients admitted by a particular physician and, given that measurement, can make judgments concerning the relative amount of inpatient resources that the physician required.

Physician economic performance evaluation provides the foundation for various cost containment strategies. It can be used simply to provide information to physicians, hospitals (HMOs, and consumers.) As set forth in the present invention, it can be linked to economic incentives in order to directly influence physician behavior. Alternate variations can be developed from the same foundation, for example, fixed rates per case for physicians. The various applications can be implemented by hospitals (as described herein), by the government, by HMOs or by consumers. All of these applications begin, however, with objective physician economic performance evaluation.

The present invention utilizes routinely collected data of the uniform bill (UB) which is issued for every patient in every acute care hospital, pursuant to federal law, and the Medicare cost report. Types of healthcare providers can be identified from the uniform bill. The types of healthcare providers can include Responsible Physician, Hospital Based Physician, such as Radiologist, Anesthesiologist, Pathologist, Consultant Physician, or Other. The identified healthcare providers provide framework for determining and comparing physician performance in each identified health provider category.

The present invention provides methodologies that can be utilized to compute physician costs (Part B) and incentive payments, based on payments to hospitals (Part A) or based on a percentage of payments to hospitals (Part A). Referred to as "Part A/B ratios", these methodologies are able to utilize payments to hospitals (Part A payments) to determine: (1) the total incentive pool of money available for rewards and incentives to physicians under a given set of constraints; (2) the total identified amount available to the various categories of healthcare providers; (3) within the pool available for payments to the Responsible Physicians, provide separate pools available for medical admissions and surgical admissions; (4) the amount of resources required by each physician to treat his/her own, case-mix adjusted for severity of illness, and (5) the best practice norm (BPN) for each patient category, such as classified by APR-DRG and for each healthcare provider category, as described above. The A/B ratios enable the method and system of the present invention to determine periodically, using hospital (Part A) data, whether a physician's performance has improved or deteriorated relative to the BPN and, under a given set of rules, the amount of reward/incentive, or compensation for loss of income, that a given physician might be entitled to. Various reports can be generated that identify problem areas and opportunities for improvement related to a given physician, at a given hospital, and with respect to a given cost center, such as room and board, radiology, operating room.

Accordingly, the present invention evaluates physician performance utilizing routinely collected data, primarily the uniform bill or hospital claim. This may be contrasted with conventional systems that attempt to accomplish the same objective utilizing other data which is usually customized for this purpose. Conventional systems are typically far more expensive, and impose significant, additional data collection burdens on providers. The method and system of the present invention is efficient, inexpensive and, because it relies on various data, ratios and categories extracted from routinely collected information, easier to implement than conventional systems. The economic physician performance evaluation methodology can be linked to financial incentives designed to (1) reward physicians that are efficient, and (2) to incent physicians that are inefficient to become efficient. For example, the present invention could be used to develop fixed case rates for physicians (similar to the case rates that Medicare currently uses to reimburse hospitals.) Alternatively, the economic physician evaluation can be used in gainsharing of physician services.

In one embodiment, the present invention relates to a method for gainsharing of physician services using a surplus allocation methodology for rewarding physicians in relation to their performance. An incentive pool is determined from previous patient claims and payments made to physicians in advance, such as in a base year. Best practice norms are established for a plurality of classified diagnosis groups. In one embodiment of the present invention, the classified diagnosis related groups are adjusted for severity of illness to compensate for actual clinical challenges faced by individual physicians. The best practice norms can be used in the surplus allocation method for determining physician performance. The incentive is established proportional to the relationship between a physician's individual performance and the best practice norm.

The amount available for distribution in the incentive pool is limited by an incentive constraint. For example, the incentive constraint can limit physician fees to twenty five percent (25%) of Part B fees associated with Medicare fee for service admissions at the Demonstration Sites, for complying with 42 CFR §417.479, Requirements for Physician Incentive Plans. This limitation, which is based upon similar restrictions applied in a conventional managed care context. The incentive constraint is designed to strike a balance such that: (1) The incentive is sufficient to overcome the natural incentives of fee for service payments to provide more services, even when medically unnecessary and (2) The incentive is not so large as to encourage a physician to withhold medically necessary services. The incentive pool is distributed by comparing current physician performance for each of the classified diagnosis related groups to the established best practice norm.

In an embodiment, the incentive pool is subdivided into incentive pools for the classified healthcare providers, such as responsible physicians, hospital based physicians and consulting physicians. The responsible physician pool is further divided into a sub pool for medical admissions and surgical admissions for the classified diagnosis related groups.

Particularly in regard to medical admissions, a physician whose resource utilization is above the Best Practice norm can be forced to sacrifice Part B income in order to implement steps to reduce hospital costs (This is because Part B fees associated with medical admissions are sensitive to length of stay, and to the professional component associated with testing). To neutralize this effect, the Part B fees that are related to follow-up physician visits that occur in regard to medical admissions, after the initial consultation, but prior to discharge are identified. The fees can be identified separately by level of severity, and multiplied by the length of stay savings projected for each level of severity, (i.e., average Base Year experience compared to Best Practice Norm). In one embodiment, the method provides an incentive pool for improvements for compensation of physicians for loss of income resulting from improvements in efficiency related to the medical admissions and improved operational performance related to surgical admissions.

While participating in the surplus allocation, physicians are directed to exercise their best clinical judgment in regard to each and every patient to maintain quality of care. In general, the system of physician performance evaluation set forth in this application is advantageous because it combines various attributes. The adjustment for severity of illness addresses a primary concern raised by physicians regarding the fairness and objectivity involved in economic performance evaluation since certain physicians attract a more difficult case-mix because of skill or reputation. The present invention uses routinely collected data. This eliminates the drawbacks of other systems which typically require the collection of data that imposes significant burden and expense on providers. The present invention directed to evaluation of physician economic performance can be linked to various payment and economic incentive systems intended to influence physician behavior.

The invention will be more fully described by reference to the following drawings.

BRIEF DESCRIPTION OF THE DRAWINGS

FIG. 7 is a schematic diagram of a generated report.

DETAILED DESCRIPTION

Figure 1:
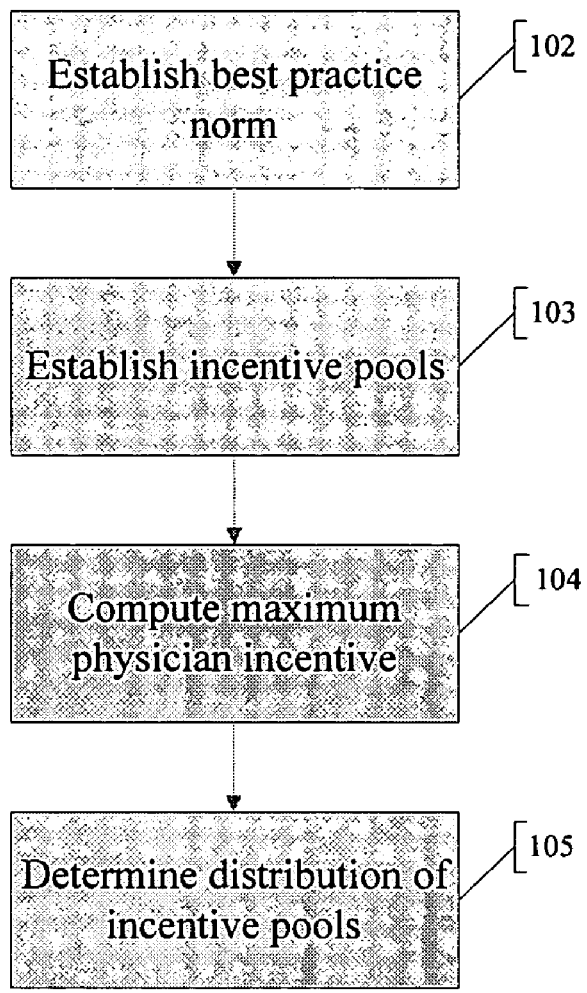
FIG. 1 is a flow diagram of a method for gainsharing of physician services.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a flow diagram of a method for gainsharing of physician services. In block 102, a best practice norm is established. The best practice norm is a standard used to identify efficient patterns of resource utilization that are achievable by a group of physicians. The best practice norm is established for a classified Diagnosis Related Group (DRG). The Diagnosis Related Groups are federally defined groupings of hospital services. The DRG can be refined for inclusion of severity of illness information, such as All Patient Related Diagnosis Related Groups (APR-DRGs), as described below. The best practice norm is used for evaluating physician performance.

Figure 2:
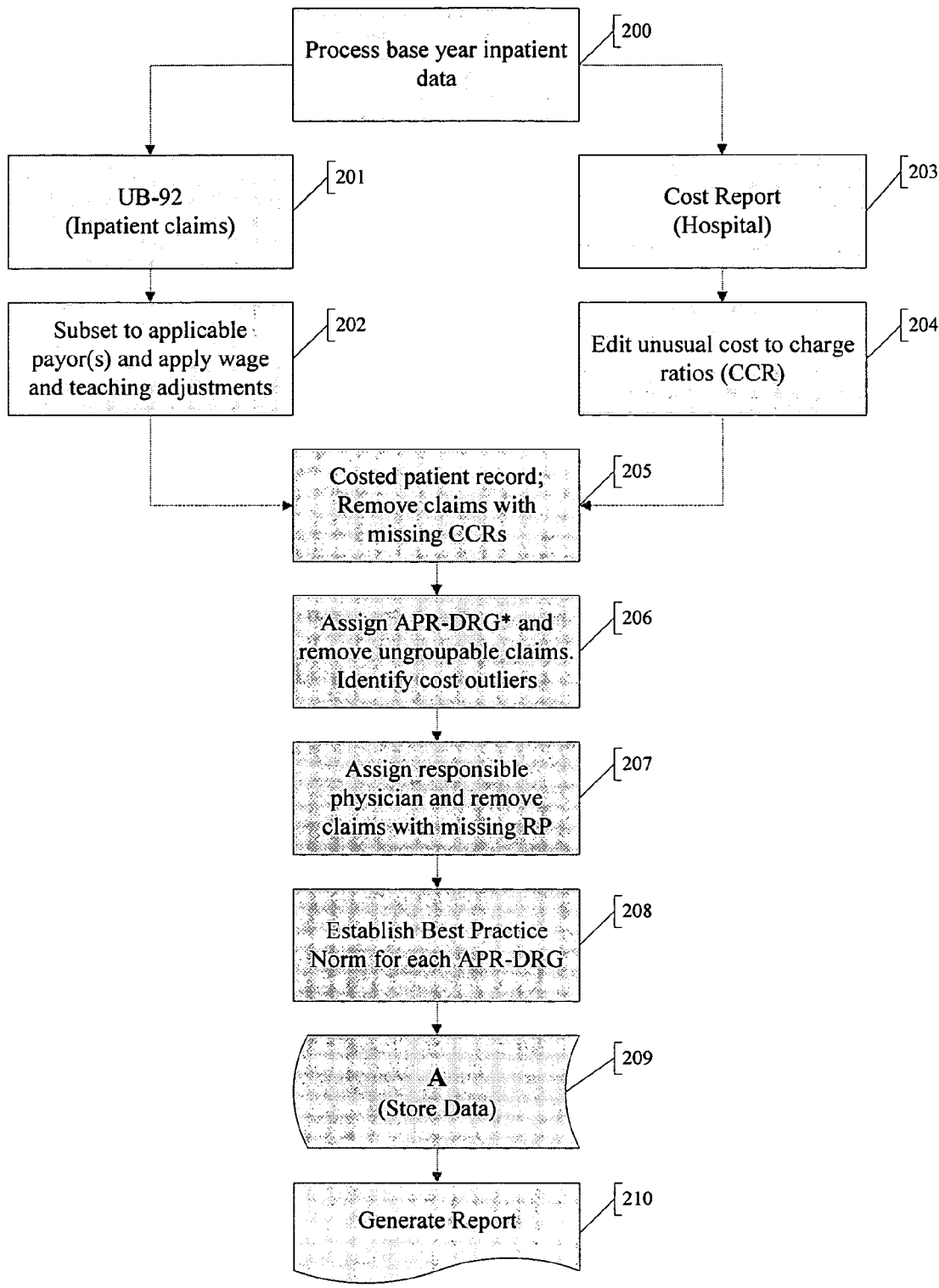
FIG. 2 is a flow diagram of a method for establishing best practice norms.

FIG. 2 illustrates an embodiment of a method for implementing block 102 for establishing best practice norms. In block 200, base year inpatient data is processed. The base inpatient data is all inpatient data for one hospital or more than one hospital in a particular grouping during a base timeframe, such as a base year. For example, the inpatient data grouping can relate to all inpatient data of all hospitals in one state, such as New Jersey or more than one state, such as the Mid-Atlantic Region. Alternatively, the inpatient data grouping can relate to inpatient data of hospitals in a portion of a state, such as hospitals in a particular county or a selected group of participating hospitals.

In block 201, base year inpatient data is determined from inpatient claim information which is generated during inpatient stays at hospitals or the like and include all claims associated with the patient's stay in the hospital, such as room and board, prescription drug claims, medical tests and the like. Inpatient claim information can be derived from claim information entered on conventional UB92 forms which are used by hospitals. In block 202, the data is subset to payors who will participate in the incentive program and edited to apply adjustments to hospitals, such as wage and teaching adjustments. For example, in order to normalize costs across a state, a wage factor such as the conventional factor employed in the Medicare inpatient prospective payment system is applied to the data to remove the wage differential that may exist across the state that may be contributing to differences in cost. In block 203, base year inpatient cost to charge ratio data is also determined from cost reports, such as the Medicare hospital cost report. In block 204, the cost report data is edited to exclude or correct outlier cost to charge ratios (CCR). In block 205, the costs incurred per inpatient claim are determined from the patient claim information and the cost reports to form a costed patient record. For example, the costs can be determined by industry standard cost accounting techniques, such as hospital-specific, cost-center-specific and ratio of costs to charges.

In block 206, the services provided in the inpatient claim are classified into diagnosis related groups. The classification of the diagnosis related groups can be adjusted for severity of illness. In the adjustment for severity of illness, the DRGs can be further defined by describing each diagnosis in terms of four levels of medical severity (refinement classes). The calculation of a severity level for each patient within a DRG considers, for example, whether the DRG is a grouping of medical or surgical diagnoses, the patient's sex, the patient's age, length of stay, whether the patient died within two days of admission, and whether the patient was discharged against medical advice. For example, an infant requiring heart surgery and intensive care for weeks is likely to place a greater drain on resources than a middle-aged victim of a minor heart attack. Even though these patients fall into the same DRG, the cost attributed to the treatment of each can be more accurately analyzed due to the refining of the DRG. In this manner, refined DRGs group patients according to resource intensity, and thus allow more accurate comparisons. For example, block 206 can be implemented for classifying Medicare fee-for-service inpatient stays by determining All Patient Related Diagnosis Related Groups using Averill, R. F. et al. Definition Manual, 3M Health Information System, Wallingford, Conn., 1988, hereby incorporated by reference into this application and as described in U.S. Pat. No. 5,652,842 hereby incorporated in its entirety by reference into this application, can be used to determine classified diagnosis related groups. It will be appreciated that in the present disclosure, classified DRGs are referred to as APR-DRGs and that APR-DRGs can refer to classified DRGs which can be determined by other patient classification methods.

In block 207, the classified services provided to a patient are assigned to a responsible physician (RP). A RP is defined as the physician most responsible for resource utilization while the patient is hospitalized. In the APR-DRG grouping, all inpatient facility claims are classified as either medical or surgical. The following two physician fields on the conventional uniform bill (UB) 92 forms can be used in the RP determination process: Attending Physician referenced by Form Locator 82 and other physician referenced by Form Locator 83. For example, the other physician can be the surgeon.

A method for the determination of the RP is as follows:

1) If the APR-DRG assigned is 469, 470, 468, 476, or 477, which are ungroupable patient DRGs, such as a procedure with unrelated diagnosis or a coding error, there is no RP assigned;

2) If the APR-DRG is surgical, the RP is the first entry in the other physician location. If the other physician location is empty, the attending physician is used;

3) If neither 1 nor 2 above apply, the RP is the attending physician;

4) If the attending physician is empty, then no RP is assigned.

In block 208, a best practice norm (BPN) is established for each classified diagnosis related group, such as each APR-DRG.

Figure 3:
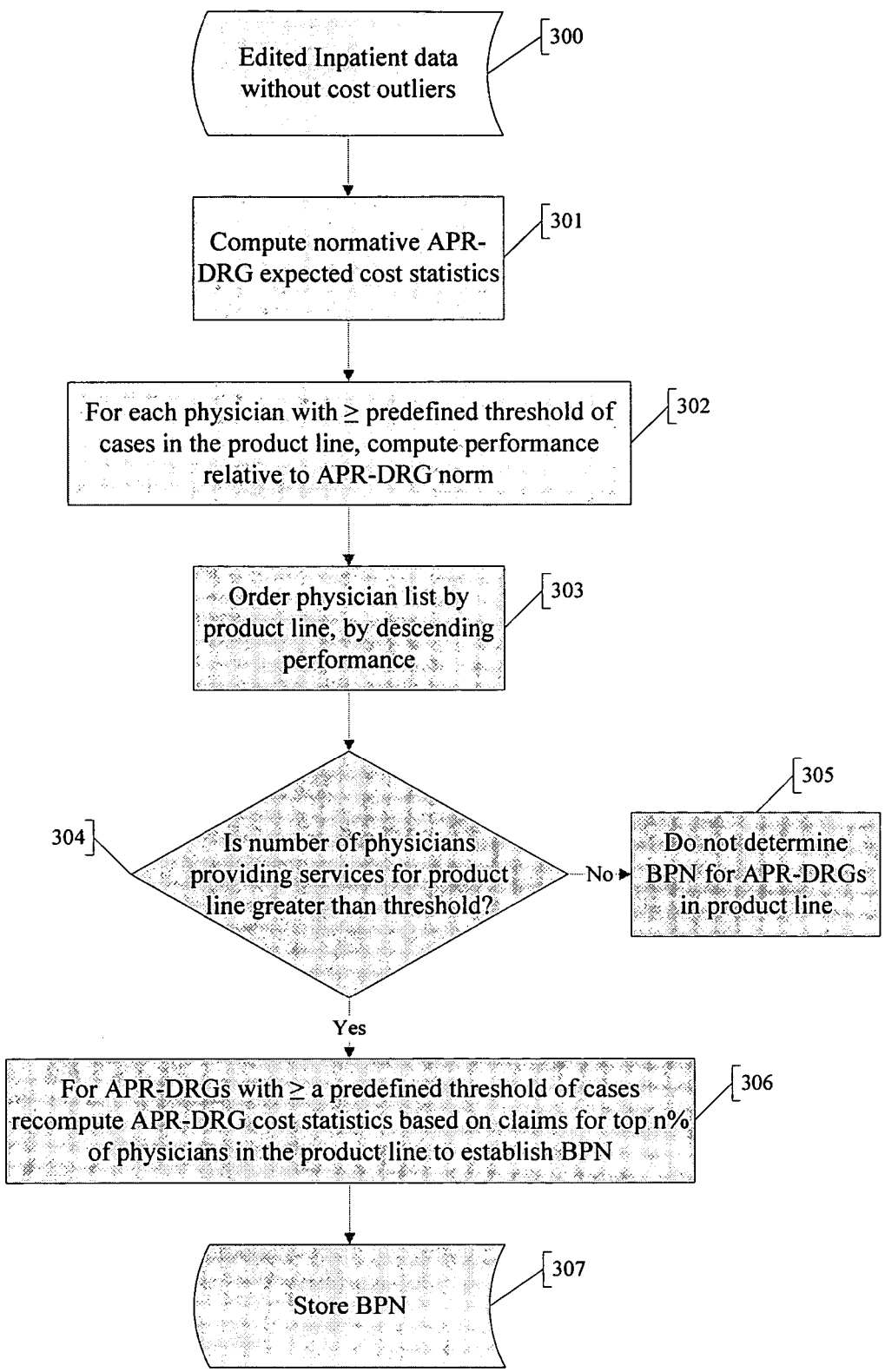
FIG. 3 is a flow diagram of a method of determining a cost statistic for a classified diagnosis related group for establishing the best practice norm.

FIG. 3 illustrates an embodiment of a method for implementing block 208 for determining a BPN. In block 300, claims with costs that are outliers (identified using conventional statistical techniques) are excluded. In block 301, a normative APR-DRG expected cost statistic is computed based on all inlier cases using the results of block 207.

In block 302, for each physician determined from inpatient data at block 300, the relationship to the APR-DRG expected cost statistic is determined. The relationship to the APR-DRG expected cost statistic for each physician can be determined by computing the percent difference of the physician's patient cost from the standard norm APR-DRG expected cost for a particular grouping of APR-DRGs, referred to as a product line. In block 302, any physician who has a number of cases within the particular APR-DRG grouping lower than a predetermined threshold of number of physician cases is excluded from the physician list. For example, the threshold of the number of physician cases can be determined to be 10 such that if the physician has less than 10 cases within the particular product line, the physician is not included in the ordered list.

In block 303, a physician list is ordered in ascending order based on the percent difference between actual cost and norm expected cost determined in block 302 such that the physician with actual cost most below the expected cost is ordered first in the list.

In blocks 304, the number of attending physicians in the selection criteria of a product line for the best practice norm is compared to a predetermined threshold of the number of physicians meeting a selection criteria best practice norm. For example, the predetermined number of physicians meeting a selection criteria best practice norm can be five attending physicians. Accordingly, if the number of attending physicians in the selection criteria is less than the threshold of the number of physicians meeting a selection criteria best practice norm, then no best practice norm is computed for that product line in block 305. An indication that the best practice norm has not been determined can be provided.

In block 306, the physicians who represent the top 'n' % of cases of within each APR-DRG grouping are selected to establish the BPN. For illustration purposes, the ordered list of physicians in an APR-DRG grouping is determined which is labeled A through Z. Starting at the first physician in the list (Physician A), the list of physicians is descended and the number of claims for each physician is accumulated until the sum of cases is equal to a predetermined threshold of physician claims. For example, the predetermined threshold of physician claims can be determined to exceed 25% of the total cases. Assuming that Physician G is the physician whose cases result in the 25% of the total cases threshold of physician claims being met, Physicians A through G define the subset of patients that are included in the best practice norm for a particular APR-DRG grouping.

If the number of attending physicians in the selection criteria for the best practice norm is greater than the threshold of the number of physicians meeting a selection criteria best practice norm, the APR-DRG cost statistic is recomputed in block 306. Using the subsets of patients defined in blocks 300-305, assigned to a physician on the ordered list whose cases meet the threshold of the number of physicians, the threshold of physician claims and the threshold of the number of physicians meeting the selection criteria best practice norm, the norm value for each APR-DRG cost statistic is recomputed. In essence, the attending physicians with the best performance (i.e., most below expected value) are used to recompute the best practice norm value for expected cost of the APR-DRG.

The BPN can be determined only if a minimum number of cases exist for each APR-DRG. For example, a BPN can be determined if there are at least 3 cases for a particular APR-DRG.

Referring to FIG. 2, data A is collected for the determined BPN from block 307 of FIG. 3. In block 209, data A is stored.

In block 210, the data is presented. For example, the data can be presented by generating a report for visually displaying data A.

Referring to FIG. 1, a surplus allocation methodology is implemented in block 103 for establishing incentive pools, in block 104 for computing the maximum physician incentive and in block 105 for determining distribution of the incentive pools.

Figure 4:
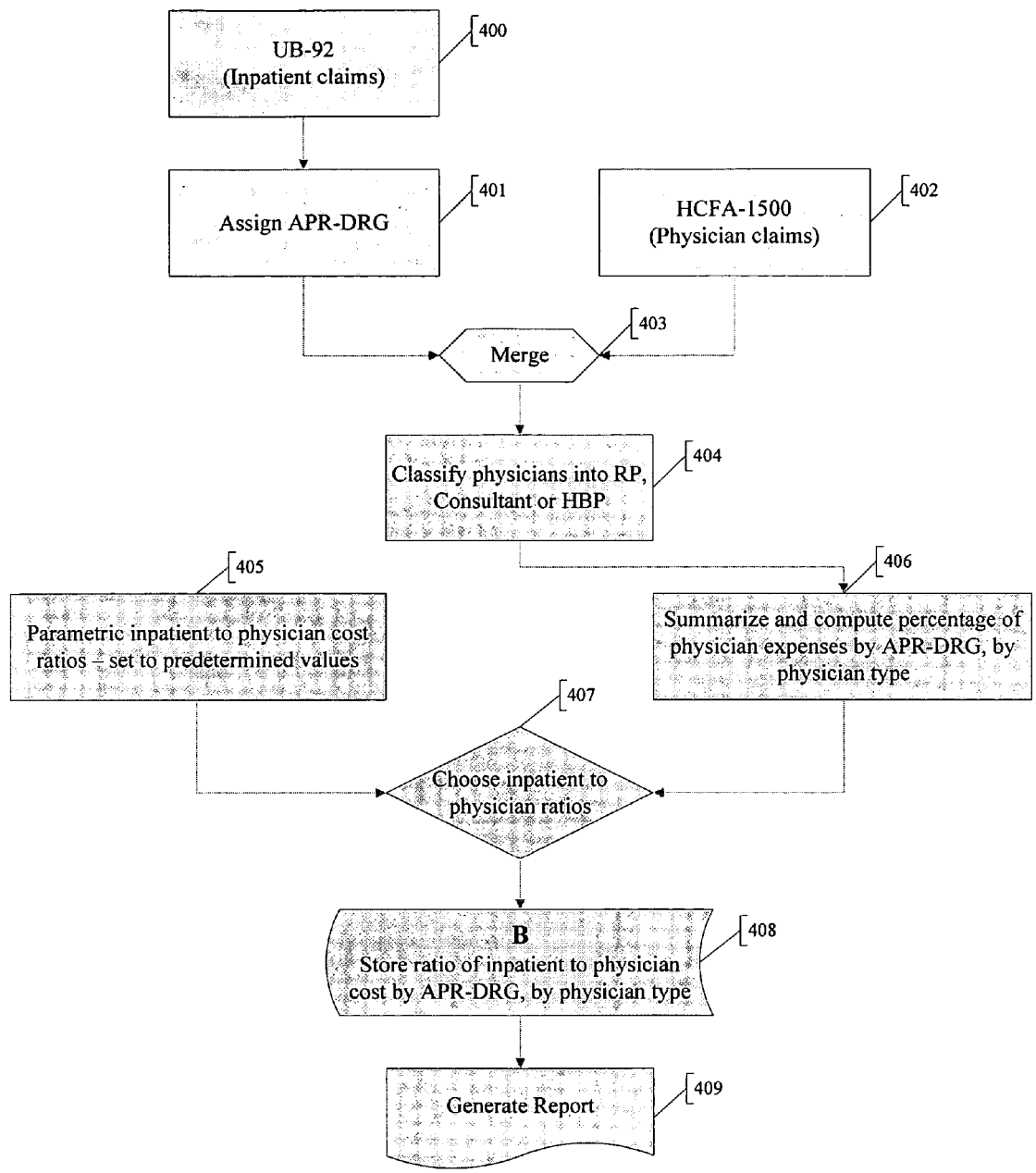
FIG. 4 is a flow diagram of a method for calculating healthcare provider type percentages to be used in establishing incentive pools.
Figure 5:
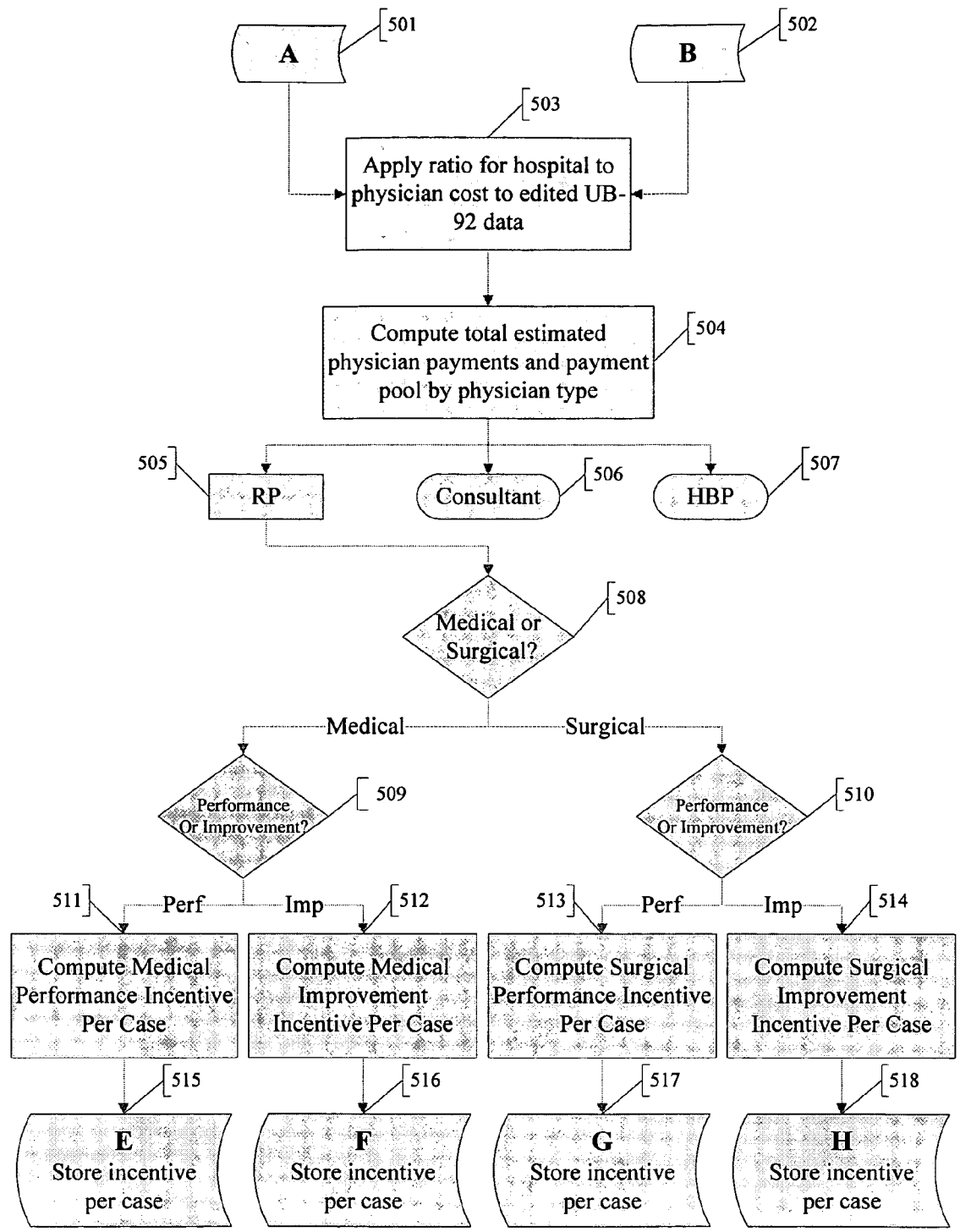
FIG. 5 is a flow diagram of a method for determining incentive pools.

An implementation of block 103 and 104 for establishing incentive pools is shown in FIG. 4 and FIG. 5. FIG. 4 illustrates a method for calculating physician type percentages, such as percentages of responsible physician (RP), consultant physician (CP) and hospital based physician (HBP), which is determined by the APR-DRG. The HBP can comprise laboratory, radiology and anesthesiology.

In block 400, inpatient claims are directed as input to block 401. In block 401, the inpatient claim is classified into a DRG refined to include severity of illness, such as an APR-DRG.

Physician bills from block 402 associated with an inpatient claim are directed as input to block 403. For example, physician bills are represented on Health Care Financing Administration (HCFA) 1500 claim forms. Block 403 links the classified patient claim data from block 401 with associated physician billing from block 402.

In block 404, merged data of the physician billing data and the classified inpatient claim data are assigned to one of the classes of physicians such as RP, CP or HBP. An implementation of block 404 is as follows:

Hospital Based Physicians (HBP) are determined as all physicians who perform a surgical procedure, including operative manual methods, incisions(s) of the body, internal manipulation and/or removal of diseased organ or tissue and can be determined as all physicians from the Anesthesiology department with a surgical CPT code between 10000 and 69999 that are associated with a surgical procedure. These physician line items can be categorized as "anesthesia hospital based physicians". HBP are also determined as all physicians from the Radiology department who use ionizing radiation, radioactive substance or magnetic resonance in the diagnosis and treatment of disease and can be determined as all physicians with a CPT code between 70000 and 79999 or between 93000 and 93550. These physician line items can be categorized as "radiology hospital based physicians". HBP are also determined as all physicians from the Pathology and Laboratory department who perform scientific studies on blood, body fluids, tissue and microscopic organisms for the purpose of diagnosis of illness and disease and can be determined as all physicians with a CPT code between 80000 and 89999. These physician line items can be categorized as "pathology hospital based physicians". HBP are also determined as all other physician line items that do not meet the above criteria that have the same physician ID that has been identified as a hospital base physician. These physician line items can be categorized as "other hospital based physicians".

If the responsible physician can not be determined from the attending physician referenced by Form Locator 82 and other physician referenced by Form Locator 83, Responsible Physician (RP) on Surgical claims can be determined when there is only one physician with a surgical CPT code (10000-69999) that has not been already identified as an Anesthesiologist. The physician's line items can be labeled as RP. When there is more than one physician associated with an inpatient admission who performs a surgical procedure, including operative manual methods, incisions(s) of the body, internal manipulation and/or removal of a diseased organ or tissue and can be determined as all physicians with a surgical CPT code (10000-69999) that has not been already identified as an Anesthesiologist, the physician with the highest charges is identified as the RP. When there is more than one physician associated with an inpatient admission who performs with a surgical CPT code (10000-69999) that has not been already identified as an Anesthesiologist and all of these physicians have the highest charges, the physician with the most number of CPT codes is identified as the RP.

Responsible Physician (RP) on Medical Claims in which treatment which does not require surgical intervention in the provision of care are determined when there is only one physician not already identified as a HBP or CP. The physician's line items are labeled as RP. When there is more than one physician not already identified as a HBP or CP, the physician with the highest number of CPT codes is identified as RP surgical claims or as medical claims.

In situations when more than one physician can be identified as the RP, the claims can go through an external review and a manual assignment of the RP can be determined.

Consulting Physicians (CP) are determined as physicians who provide expertise in one or more specialties to the responsible physician when such expertise is outside the responsible physician's area of expertise and can be determined as all physicians with all line items with a CPT code between 99251 and 99274 and not already identified as a HBP. Also, after the RP and HBP been assigned, the remaining physician line items are identified as CP.

In block 405, parametric ratios are input. In the parametric approach, two sets of ratios are established: (1) The total amount available for incentive payments to physicians may be set at X % of savings, as measured by the previously described methodology. Payments to individual physicians under this scenario would be determined in the same way as previously described. (2) Similarly, payments to the participating third party payor (e.g. HMO, managed care company, etc) would also be determined as a percentage of savings, as measured by the previously described methodology. The parametric ratios are designed to allow for such implementation scenarios. In block 406, hospital to physician ratios are computed based on the ratio of expenses from physician claims from block 402 to hospital expenses from block 400. These ratios are computed by each classified DRG, such as APR-DRG. In block 407, one of the two approaches to setting the hospital to physician ratios is selected.

Data B in block 408 is the stored % RP, CP and HBP by APR-DRG and the ratio of physician to hospital expenses. In block 409, the data is presented. For example, a report can be generated of the break down of percentages for the types of physicians.

FIG. 5 is an implementation of block 103, a method for determining incentive pools. In block 503, the ratios from data B are applied to the costed hospital data A. In block 504, the total estimated physician payments, such as Part B payments are determined by applying the A/B ratio to the total Part A payments. A total physician incentive pool is determined to be consistent with an incentive constraint. For example, the Part B fees can be limited to an incentive constraint of 25% to be consistent with 42 C.F.R. § 417.479 requirements for incentive plans, as described above.

Data B of the % RP, CP and HBP by APR-DRG is applied to the total physician pool to distribute the incentive pool between determined types of physicians RP, CP and HBP in respective blocks 505, 506 and 507. In block 508, the determined RP incentive pool is proportioned between a medical incentive pool and a surgical incentive pool. In block 509, a loss of income (LOI) pool is subtracted from the total RP incentive pool. In block 512, the LOI is used in an improvement pool at each level of severity to reimburse physicians for loss of income resulting from improvements in efficiency related to the medical admissions. The balance left in the RP incentive pool is divided between a medical performance pool of block 511 and a surgical incentive pool of block 510. The amount of distribution into the medical performance pool and the surgical incentive pool can be based on a ratio of the total medical RP fees received to the total surgical RP fees received.

In block 511, a maximum medical performance incentive per case is determined for each classified DRG, such as APR-DRG, based on relative cost of each APR-DRG.

Data E of the maximum medical performance incentive per case is stored in block 515. In block 512, a maximum medical improvement incentive is determined as improvement in operational performance for each classified DRG, such as APR-DRG. Data F of the maximum medical improvement incentive per case is stored in block 516.

Block 510 apportions a surgical performance pool of block 513 with a surgical improvement pool of block 514. For example, the surgical incentive pool of block 510 can be divided in half with 50% being used in the surgical performance pool of block 513 and 50% being used in the surgical improvement pool of block 514. In block 513, a maximum surgical performance incentive is determined by each classified DRG, such as APR-DRG, based on relative costliness to other APR-DRGs. Data G of the maximum surgical performance incentive per case is stored in block 517. In block 514, a maximum surgical performance incentive is determined by improvement in operational performance for each classified DRG, such as APR-DRG. Data H of the maximum surgical improvement incentive per case is stored in block 518.

The proportional amounts set aside in the LOI for the medical improvement incentive pool can be reduced over time as efficiency of physician increases under method 10. For example, initial amounts set aside in the medical improvement pool and the surgical improvement pool can be reduced to 75% in the second year of implementation of method 10 and 50% in the third year of implementation of method 10 with the 25% subtracted medical improvement pool and surgical improvement pool being added to the medical performance pool and the surgical performance pool, respectively.

The following is an example of an implementation for determining incentive pools:

EXAMPLE 1

1. Total Part A payments at 13 hospitals=$695,480,857. Apply Part A/B ratios to determine total Part B payments, and apply 25% limit to determine total pool available for incentive payments to physicians ($33,314,292).
2. Utilize RP identifiers and Part A/B ratios to determine amount of total incentive pool available for distribution to Responsible Physicians ($22,561,127).
3. Estimate payments for loss of income: Identify specific dollar amounts for physician inpatient visits (after initial consult, but prior to discharge) associated with medical admissions, by level of severity. Multiply fees by LOS savings projected for each level of severity and sum: $7,071,702.
4. Subtract projected LOI ($7,071,702) from total pool available for distribution to RPs ($22,561,127) to determine total Performance Pool: $15,489,425.
5. Apply Part A/B ratios to separate Part B payments to Responsible Physicians into:
   Medical: $30,037,866
   Surgical: $60,206,642
   (Ratio of medical to surgical payments is 1 to 2)
6. Utilize ratio of Part B payments determined in Step 5 to divide total Performance Pool into Performance Pool/Medical=$5,155,651; and Surgical Pool=$10,333,741.
7. Split Surgical Pool into two equal pools: Improvement Pool/Surgical=$5,166,887; and Performance Pool/Surgical=$5,166,887. (Determine Maximum Physician Incentive for both Performance Pools <medical and surgical> by allocating to APR DRGs based on relative costliness.)
8. Convert LOI set aside ($7,071,702—Step 4) into Improvement Pool/Medical. (Total Pool Available=$22,561,127, less LOI (Improvement Pool/Medical) $7,071,702, less Surgical Pool $10,333,741, results in Performance Pool/Medical of $5,155,651—Step 6.)
9. Both Medical and Surgical Improvement Pools can be phased out: Year 1-100%; Year 2-75%; Year 3-50% and so forth until the Improvement Pool is merged entirely into the Performance Pool; and the sums subtracted and merged into the respective Performance Pools.

Figure 6A:
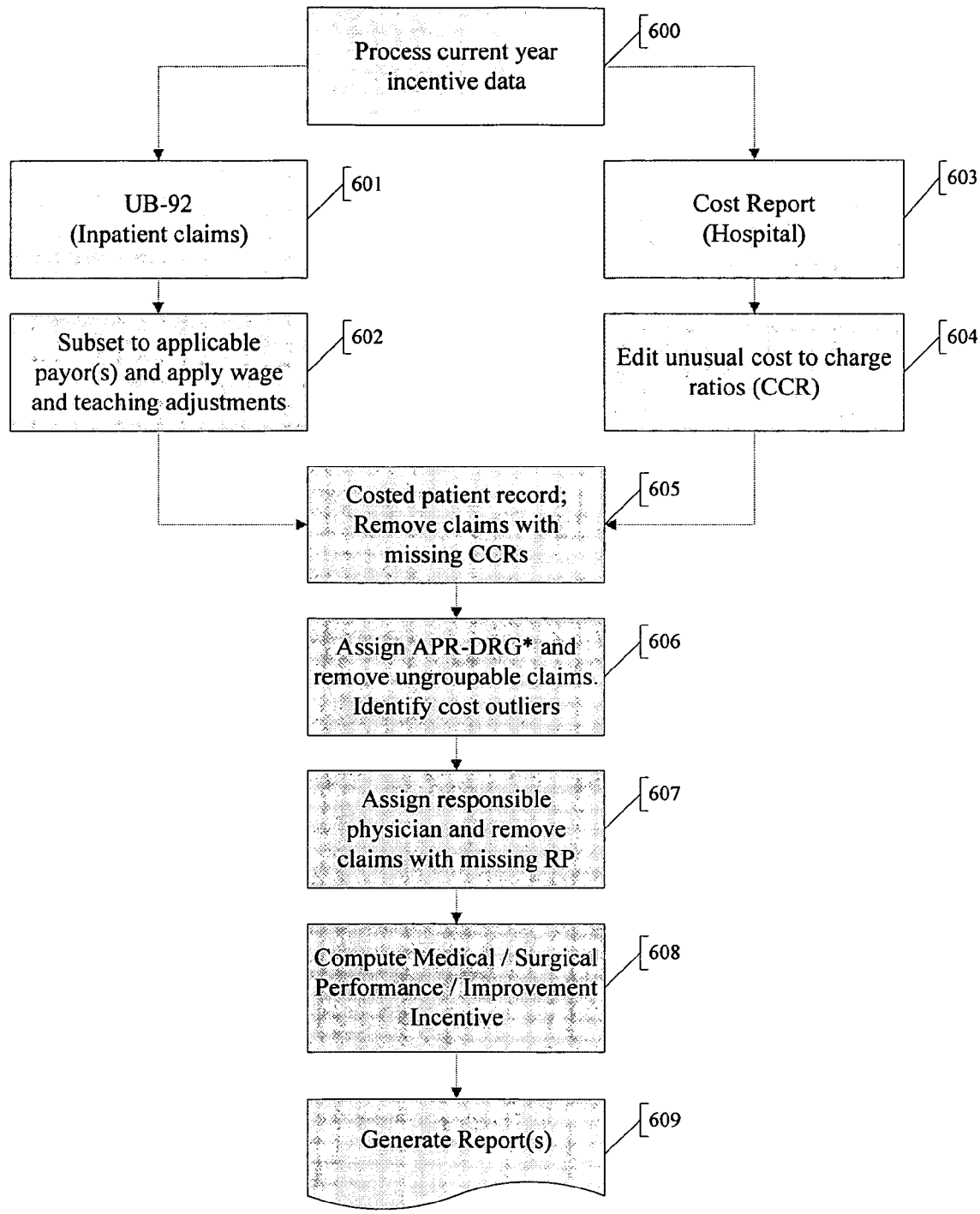
FIG. 6A is a flow diagram of a method for distributing incentive pools.

An implementation of block 106 for distributing of an incentive pool determined for a responsible physician is shown in FIG. 6A. In block 600, current year inpatient data is processed. In block 601 inpatient claim information, such as information entered on a conventional UB 92 form is processed. In block 603, current year inpatient data is also determined from hospital cost reports.

In block 602, the inpatient claims are subset to payors who will participate in the incentive program and edited to apply adjustments to hospitals such as wage and teaching adjustments. In block 604, the current year cost report data is edited to exclude or correct outlier cost to charge ratios.

In block 605, the costs incurred per patient claim are determined to form a costed patient record. For example, the costs can be determined by industry standard cost accounting techniques such as hospital-specific, cost-center-specific and ratio of costs to charges.

In block 606, the services provided in the inpatient claim are classified into diagnosis related groups. The classification of the diagnosis related groups can be adjusted for the severity of illness. For example, block 606 can be implemented for classifying Medicare fee-for-service inpatients by determining All Patient Related Diagnosis Related Groups using Averill, R. F. et al., Definition Manual, 3M Health Information System, Wallingford, Conn., 1988, hereby incorporated by reference into this application. In block 607, the classified services provided to a patient are grouped by responsible physician (RP). The identity of the RP can be determined as described above in reference to block 207. In block 608, the incentive is computed. Detailed descriptions of the computation of incentives are in FIGS. 6B-6D.

The identity of the admissions for the RP are determined to be medical or surgical based on the APR-DRG.

Figure 6B:
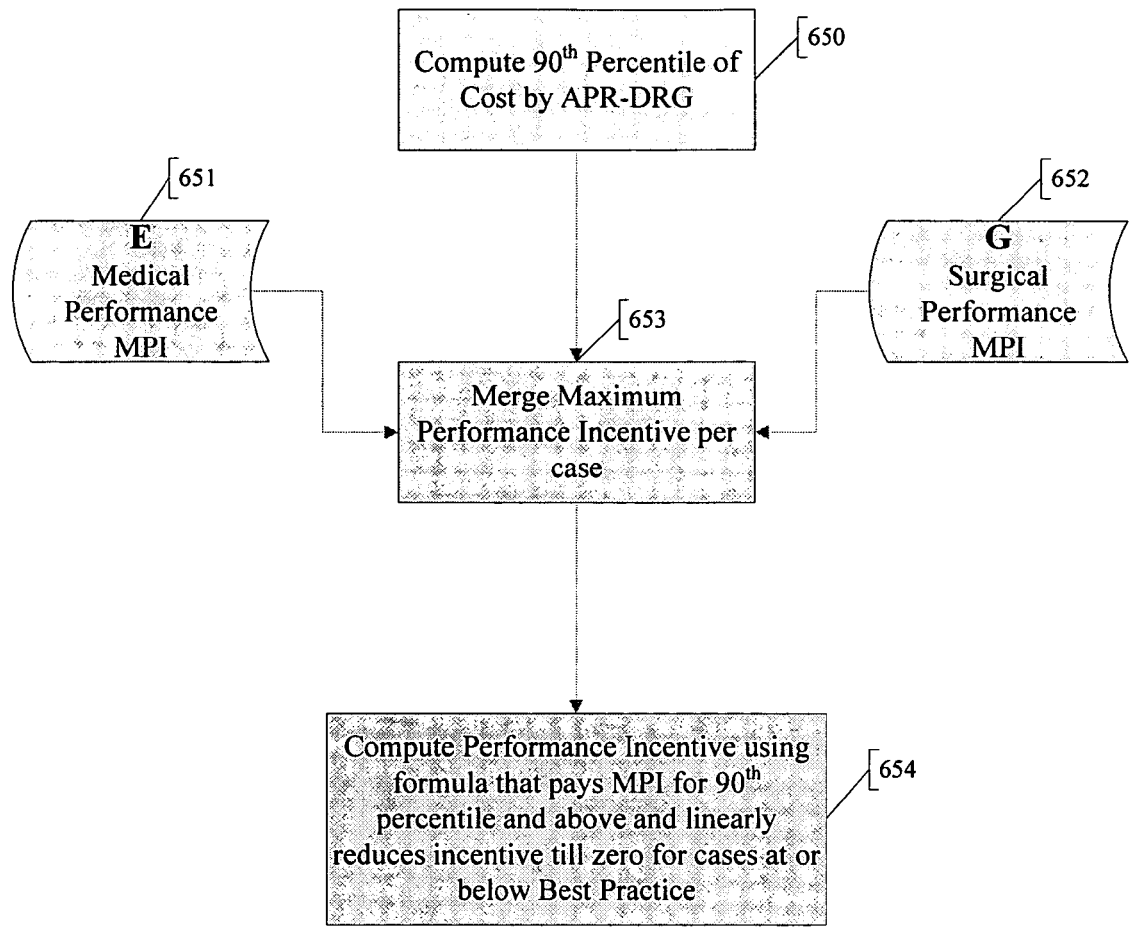
FIG. 6B is a flow diagram of a method for computing the maximum physician incentive by classified diagnosis group.
Figure 6C:
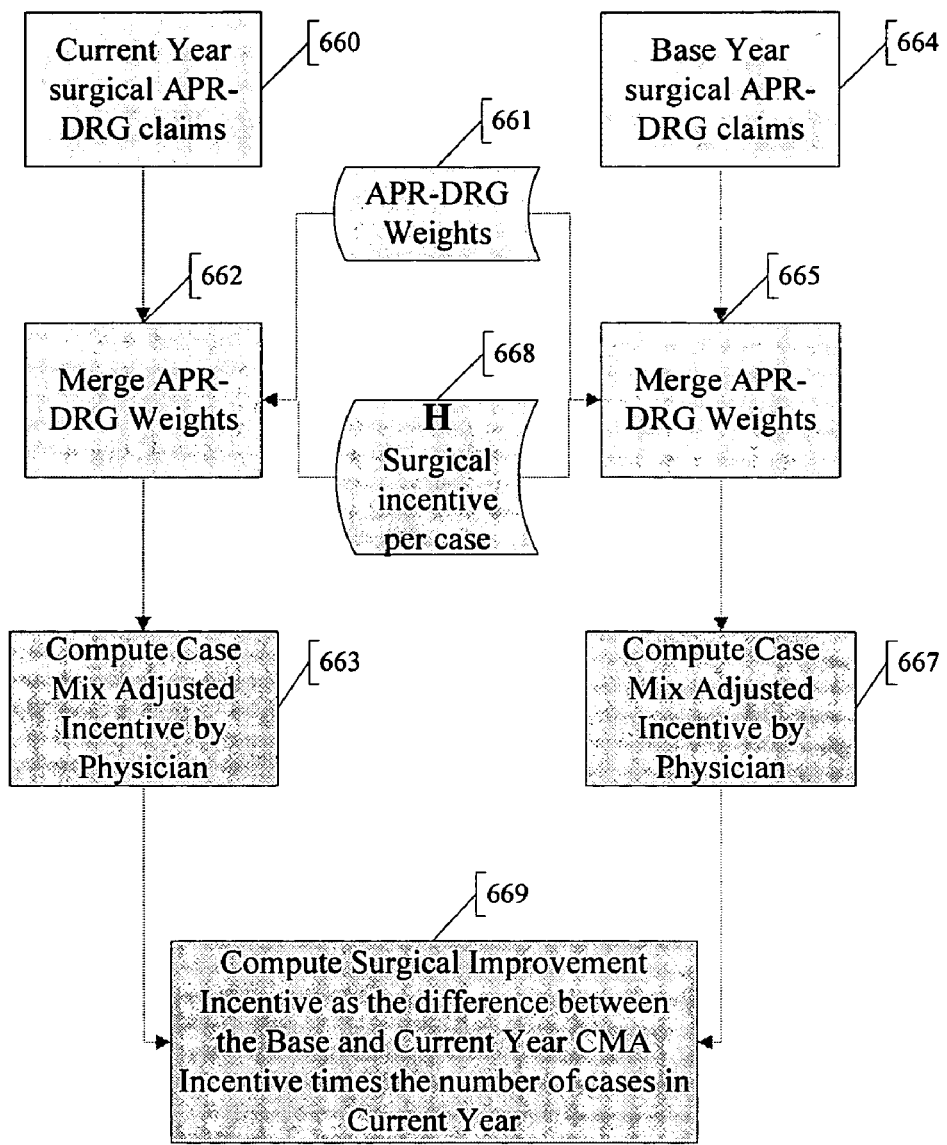
FIG. 6C is a flow diagram of a method for computing the surgical improvement incentive.

In FIG. 6B, the performance incentives for the medical and surgical RP is determined using data A related to the best practice norm. A performance ratio is determined as the ratio of the individual RP performance to the best practice norm. A performance threshold can be determined to allow all physicians to receive payments if their performance ratio is greater than the performance threshold.

In block 654, a performance incentive is calculated using data E or G of the maximum performance per case and the performance ratio from block 650. In one embodiment, the performance threshold can also include a threshold of the number of patients admitted per physician. For example, a physician will not meet the performance threshold if the physician admits less than 10 patients in the current year. The maximum medical performance per case is not available to the RP if the physician's performance is determined to be lower than the performance threshold. For example, the performance threshold can relate to physicians at or below a percentile of physicians, such as the 90$^{th}$ percentile of physicians. An example of a determined incentive can be determined as follows:

$$\frac{\text{Percentile Cost} - \text{Physician's Actual Cost}}{\text{Percentile Cost} - \text{Best Practice Cost}} \times \text{Maximum Physician Incentive}$$

In FIG. 6B, the improvement incentive for the surgical RP is determined using the case mix adjusted surgical improvement incentive per case. In order to account for differences in the mix of cases between years contributing to an improvement, the improvement incentive is case mix adjusted using a standard set of weights such as the APR-DRG weights shown in block 668. The case mix adjusted incentive computed in block 663 and 667 are compared and the difference is computed in block 669.

Figure 6D:
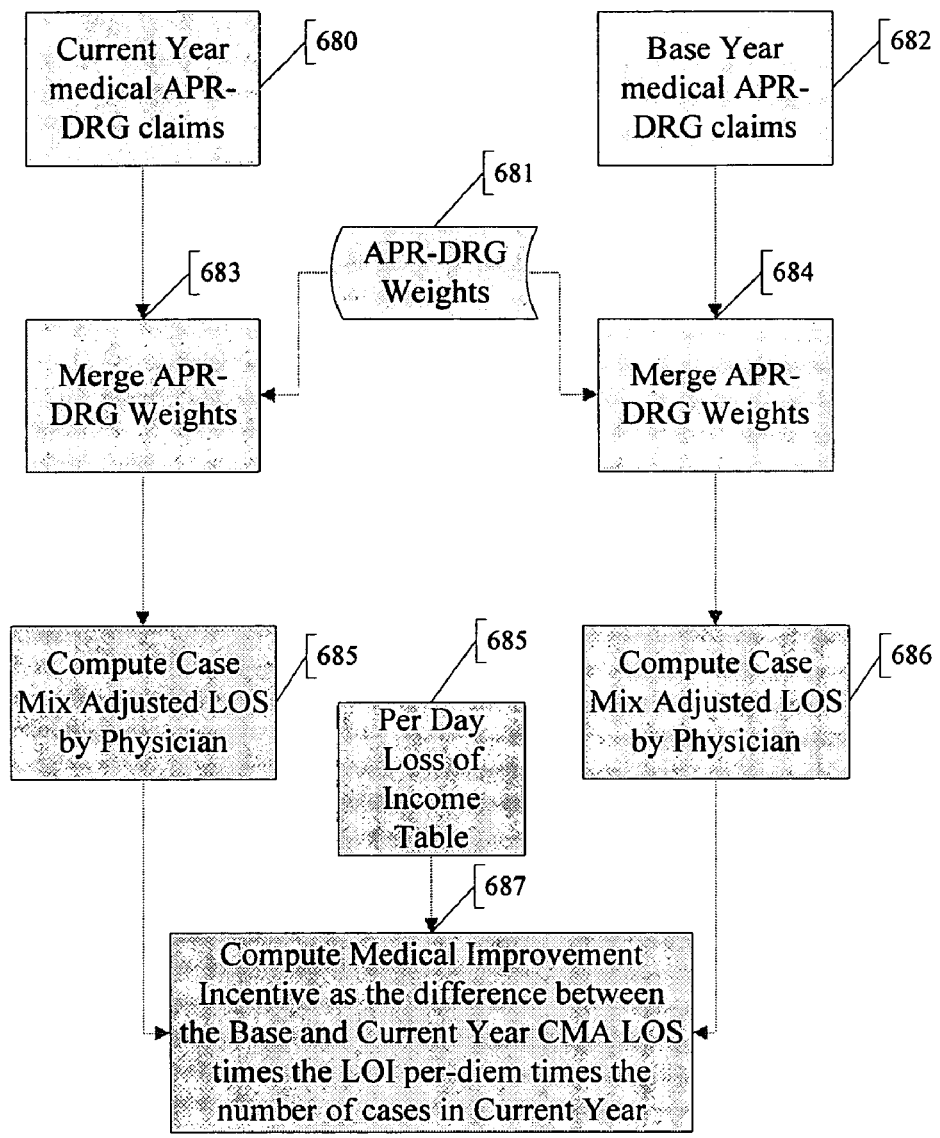
FIG. 6D is a flow diagram of a method for computing the medical improvement incentive or loss of income compensation.

In FIG. 6D, a medical improvement incentive is calculated using a determination of improvement in operational performance. The improvement incentive can be determined by case mix adjusted changes in cost to determine an improvement ratio. Data F is related to the changes in Part B income from changes in inpatient cost driven by length of stay (LOS) determined by:

(Base Year LOS–Actual Year LOS)×Per Diem×Percentile

In order to account for differences in the mix of cases between years contributing to a difference in LOS, the LOS in each year is case mix adjusted using a standard set of weights such as the APR-DRG weights shown in block 681. The case mix adjusted LOS computed in block 685 and 686 are compared and the difference is multiplied by the per day loss of income table from block 685. The per day loss of income table can be from a source such as the Medicare Part-B Physician/Supplier RBRVS based fee schedule published by CMS.

The medical performance incentive determined from block 654 and the medical improvement incentive determined from block 687 are totaled to determine a total medical incentive.

The distribution of an incentive pool determined for a consultant physician and a hospital based physician can be determined in the similar manner as described with regard to the distribution of the incentive pool determined for a responsible physician. Alternatively, the incentive pool determined for a consultant physician and a hospital based physician can be determined by discretion, for example by the responsible physicians, hospital or payer.

The following is an example of distribution from medical performance pool and the surgical performance pool:

EXAMPLE 2

Performance Pool/Surgical*

| Assume: | 90$^{th}$ Percentile= | $33,709 |
|---|---|---|
| | Best Practice Norm= | $15,500 |
| | Maximum Physician Incentive= | $280 |
| | Surgeon A actual cost= | $15,500 |
| | Surgeon B actual cost= | $18,877 |
| | Surgeon C actual cost= | $26,967 |

-continued

| Surgeon | Perf $ | |
|---|---|---|
| A= | $280 | $33,709 − $15,500 = $18,209 |
| | | $33,709 − $15,500 = $18,209 × $280 |
| B= | $228 | $33.709 − $18,877 = $14,832 |
| | | $33,709 − $15,500 = $18,209 × $280 |
| C= | $104 | $33,709 − $26,967 = $6,742 |
| | | $33,709 − $15,500 = $18,209 × $280 |

Performance Pool/Medical*

| Assume: | 90$^{th}$ Percentile= | $12,000 |
|---|---|---|
| | Best Practice Norm= | $6,000 |
| | Maximum Physician Incentive= | $120 |
| | Physician A actual cost= | $6,000 |
| | Physician B actual cost= | $7,000 |
| | Physician C actual cost= | $10,000 |

| Physician | Perf $ | |
|---|---|---|
| A= | $120 | $12,000 − $6,000 |
| | | $12,000 − $6,000 = 6/6 × $120 |
| B= | $100 | $12,000 − $7,000 |
| | | $12,000 − $6,000 = 5/6 × $120 |
| C= | $40 | $12,000 − $10,000 |
| | | $12,000 − $6,000 = 2/6 × $120 |

In block 609, a physician report of the total incentive is generated. An example of a physician report is shown in FIG. 7.

Figure 8:
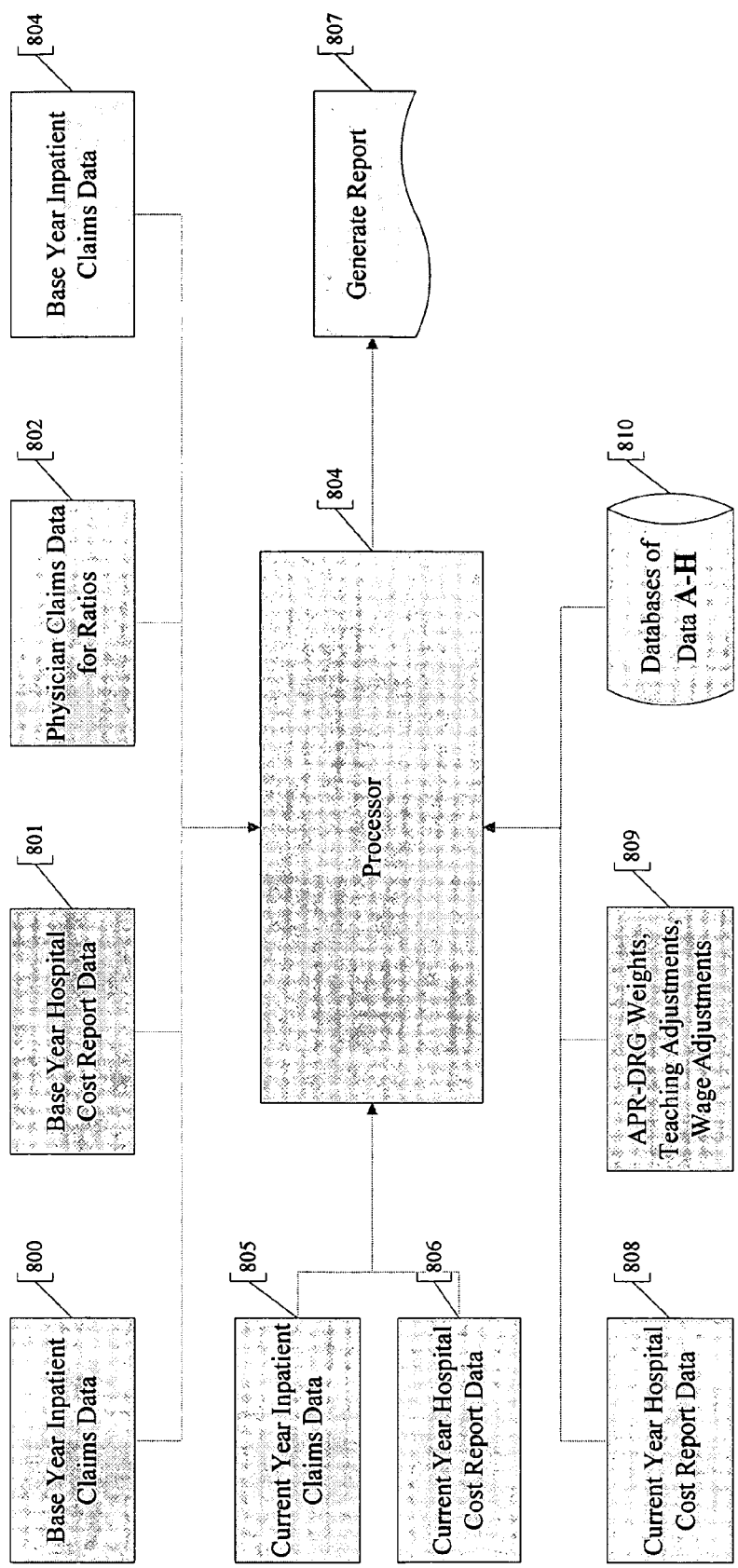
FIG. 8 is a schematic diagram of a system for implementing the method of gainsharing of physician services.

FIG. 8 illustrates a schematic diagram of the system for implementing method 10. Base inpatient claim data 800, base cost report hospital data 801 and base physician billing data 802 are provided to processor 804. Processor 804 is controlled by programming information to implement all steps in method 10. Base inpatient claim data 800 is used in block 200 and block 400 of method 10. Base cost report hospital data 801 is used in block 203 of method 10. Base physician billing data 802 is used in block 403 of method 10.

Current inpatient claim data 805 and current hospital cost report data 806 are provided to processor 804. Current inpatient claim data is used in block 601 of method 10. Current hospital cost report data is used in block 603 of method 10.

One or more databases 810 store data A, data B, data C, data D, data E, data F, data G and data H. One or more reports 807 are generated by method 10 and provided by processor 804. Reports 807 can be generated by block 210, block 409, and block 609 of method 10.

Ancillary weights, adjustments and parameters to the processor 804 are shown in block 809.

Figure 9:
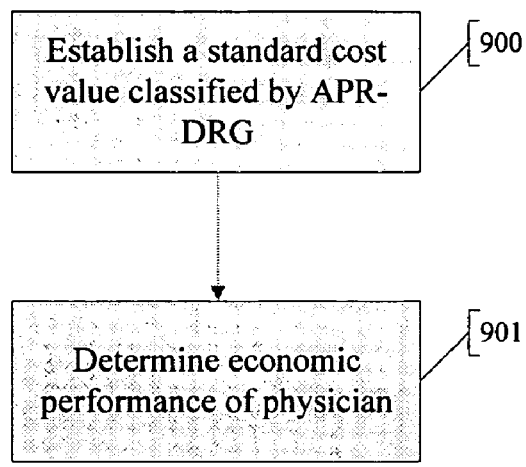
FIG. 9 is a flow diagram of a method for evaluating physician economic performance.

FIG. 9 is a flow diagram of a method for evaluating economic performance of a physician. In block 900, a standard cost value is determined from data of an All Patient Referral Diagnosis Related Group. In one embodiment, the standard cost value is established as a best practice norm as described above. In this embodiment, block 901 can be implemented with blocks from FIG. 2 and blocks from FIG. 3, as described above. In block 901, economic performance of a physician is determined.

Figure 10:
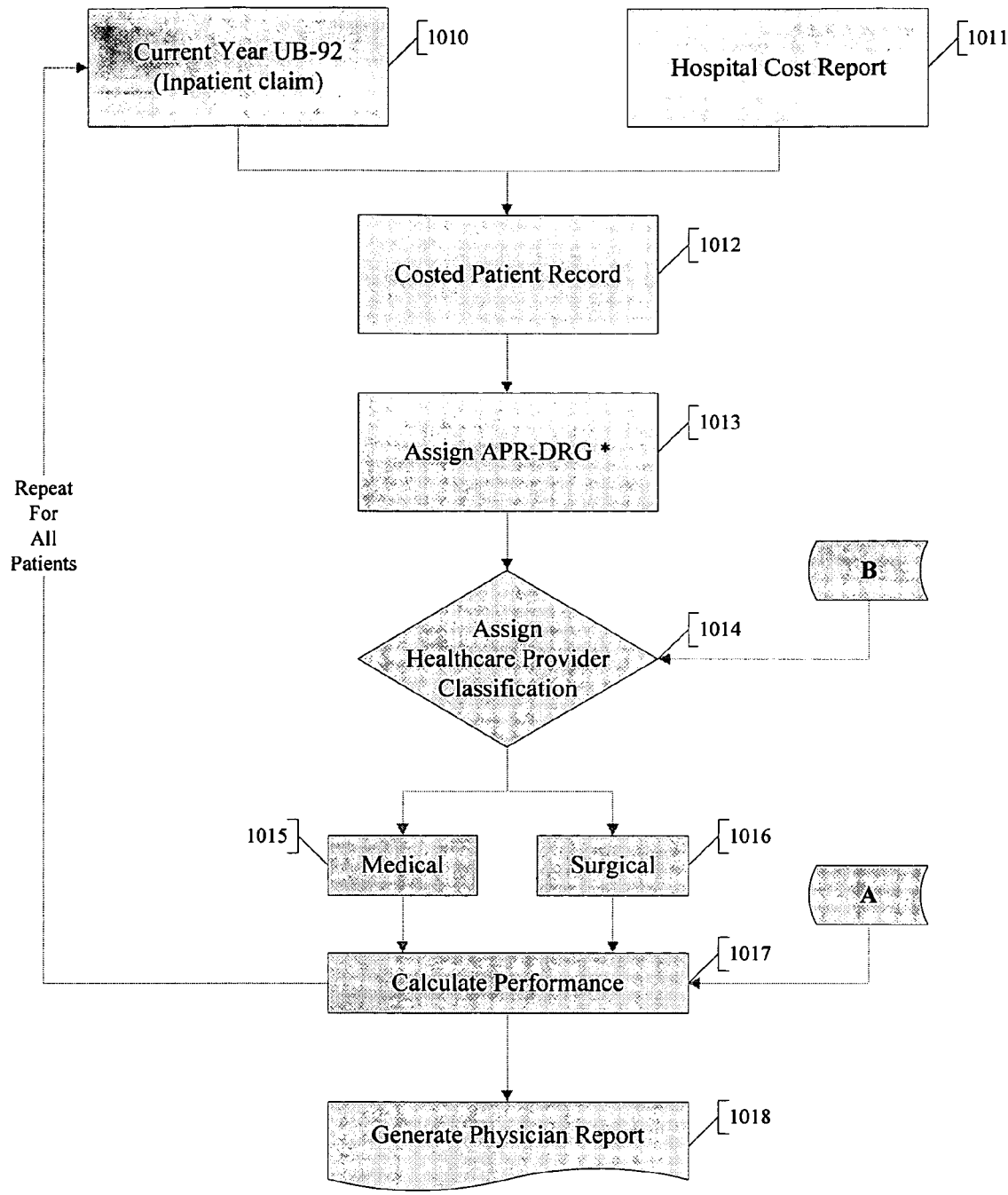
FIG. 10 is a flow diagram of a method for determining physician economic performance used in FIG. 9.

An implementation of block 901 for determining economic performance of a physician is shown in FIG. 10. In block 910, current year inpatient data is determined from inpatient claim information, such as information entered on a conventional UB 92 form. In block 911, current year inpatient data is also determined from hospital cost reports. In block 912, the costs incurred per patient claim are determined to form a costed patient record. For example, the costs can be determined by industry standard cost accounting techniques such as hospital-specific, cost-center-specific and ratio of costs to charges.

In block 913, the services provided in the inpatient claim are classified into diagnosis related groups. The classification of the diagnosis related groups can be adjusted for the severity of illness. For example, block 913 can be implemented for classifying Medicare fee-for-service inpatients by determining All Patient Related Diagnosis Related Groups using Averill, R. F. et al., Definition Manual, 3M Health Information System, Wallingford, Conn., 1988, hereby incorporated by reference into this application. In block 914, the classified services provided to a patient are assigned to a healthcare provider classification. For example, data B 54 of the % RP by APR-DRG, % CP by APR-DRG and % HBP by APR-DRG can be used to determine a RP, CP or HBP provider type, as described above. The identity of the admissions for the classified healthcare provider are determined to be medical in block 915 or are determined to be surgical in block 916.

In block 917, the performance of a healthcare provider for a medical admissions of a healthcare provider is determined using data A 27 related to the best practice norm. In block 918, the performance of a healthcare provider for a surgical service is determined using data A 27 related to the best practice norm. A performance ratio is determined of the individual RP performance to the best practice norm. Each of blocks 910-918 are repeated as needed for all patients.

In block 919, a physician report of the economic performance of one or more physicians for a medical service is generated. In block 920, a physician report of the economic performance of one or more physicians for a surgical service is generated.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A method capable of providing gainsharing of physician services for a plurality of physicians comprising the steps of:
    (a) identifying a population comprising a plurality of patients;
    (b) for each patient, receiving by a computer one or more inpatient admission charges for medical services rendered to the respective patient;
    (c) for each inpatient admission charge, adjusting by a computer the inpatient admission charge by a severity of illness experienced by the respective patient during provision of the medical services;
    (d) defining a plurality of All Patient Refined Diagnostic Related Groups, wherein each All Patient Refined Diagnostic Related Group is statistically homogenous group of similar medical charges;
    (e) for each inpatient admission charge:
        (i) categorizing by a computer the inpatient admission charge into the All Patient Refined Diagnostic Related Groups based on the inpatient admission charge's designated medical diagnosis;
        (ii) identifying the physician responsible therefor;
    (f) for each All Patient Refined Diagnostic Related Group:
        (i) defining a numeric threshold;
        (ii) filtering by a computer from the All Patient Refined Diagnostic Related Group all inpatient admission charges not below the numeric threshold;
        (iii) using the billed amounts of the filtered inpatient admission charges below the threshold to determine a best practice norm;
    (g) identifying a plurality of physicians participating in the gainsharing program;
    (h) for each physician;
        (i) assign one or more inpatient admission charges for which the physician is the responsible physician;
        (ii) grouping the physician's one or more inpatient admission charges by the respective All Patient Refined Diagnostic Related Group;
        (iii) analyzing by a computer the physician's inpatient admission charges in each All Patient Refined Diagnostic Related Group to determine a current performance profile for each respective All Patient Refined Diagnostic Related Group;
        (iv) comparing by a computer each current performance profile with the best practice norm in the appropriate All Patient Refined Diagnostic Related Group to determine the physician's performance;
        (v) determining by a computer the physician's gainsharing amount based on the physician's performance, wherein the physician's gainsharing amount is capped by a maximum amount;
    (i) repeating the method for a future period.

2. The method of claim 1, further comprising the steps of:
   determining hospital to physician cost ratios for each said All Patient Refined Diagnosis Related Groups from either parametric ratios or hospital to physician cost ratios computed from ratios of physician billing data and said inpatient admission charges.

3. The method of claim 2 further comprising:
   storing said physician cost ratios for each said All Patient Refined Diagnosis Related Groups.

4. The method of claim 3 further comprising:
   generating a report of said physician cost ratios for each said All Patient Refined Diagnosis Related Groups.

5. The method of claim 2 wherein said parametric ratios are determined as a first ratio of a percentage of savings for determining an amount of said incentive goal available for physician gainsharing and a second ratio of a percentage of savings for determining payments to participating third-party payors.

6. The method of claim 1 wherein said inpatient admission charges comprises current inpatient claim information and current hospital cost data.

7. The method of claim 6 wherein said inpatient admission charges is determined from a uniform bill (UB) or hospital claim.

8. The method of claim 1 further comprising the step of:
   storing data collected for said determined best practice norm.

9. The method of claim 8 further comprising the step of:
   generating a report for visually displaying said data collected from said established best practice norm.

10. The method of claim 1 further comprising the step of editing said filtered inpatient admission charges to exclude outlier hospital cost data.

* * * * *